United States Patent
Feng et al.

(10) Patent No.: US 9,717,795 B2
(45) Date of Patent: Aug. 1, 2017

(54) HPPH LYOPHILIZED POWDER INJECTION FOR INJECTION AND PREPARATION METHOD THEREOF

(71) Applicant: ZHEJIANG HISUN PHARMACEUTICAL CO., LTD, Zhejiang (CN)

(72) Inventors: Chunrong Feng, Zhejiang (CN); Huanwei Zhang, Zhejiang (CN); Jianqiao Wang, Zhejiang (CN)

(73) Assignee: ZHEJIANG HISUN PHARMACEUTICAL CO., LTD., Zhejiang (CN)

(*) Notice: Subject to any disclaimer, the term of this patent is extended or adjusted under 35 U.S.C. 154(b) by 0 days.

(21) Appl. No.: 14/765,983

(22) PCT Filed: Jan. 21, 2014

(86) PCT No.: PCT/CN2014/070974
§ 371 (c)(1),
(2) Date: Aug. 5, 2015

(87) PCT Pub. No.: WO2014/121691
PCT Pub. Date: Aug. 14, 2014

(65) Prior Publication Data
US 2015/0366965 A1    Dec. 24, 2015

(30) Foreign Application Priority Data
Feb. 5, 2013    (CN) .......................... 2013 1 0046627

(51) Int. Cl.
*A61K 31/40* (2006.01)
*A61K 41/00* (2006.01)
*A61K 9/19* (2006.01)
*A61K 31/409* (2006.01)
*A61K 9/00* (2006.01)
*A61J 3/02* (2006.01)
*A61K 9/14* (2006.01)

(52) U.S. Cl.
CPC ............ *A61K 41/0076* (2013.01); *A61J 3/02* (2013.01); *A61K 9/0019* (2013.01); *A61K 9/143* (2013.01); *A61K 9/145* (2013.01); *A61K 9/19* (2013.01); *A61K 31/409* (2013.01)

(58) Field of Classification Search
CPC .................................................. A61K 31/409
USPC ........................................................ 514/410
See application file for complete search history.

(56) References Cited

U.S. PATENT DOCUMENTS

| 7,166,719 B2 * | 1/2007 | Pandey ................ C07D 471/22 424/9.362 |
| 2010/0137396 A1 | 6/2010 | Pandey et al. |

FOREIGN PATENT DOCUMENTS

| CN | 101219137 A | 7/2008 |
| WO | 03/028628 A2 | 4/2003 |

OTHER PUBLICATIONS

International Search Report mailed Apr. 30, 2014; PCT/CN2014/070974.
Pharmaceutics; Based on the Fifth Edition chiefly edited by Cui Defu, p. 83, the last paragraph, People's Health Publishing House, published in Mar. 2004.
First Chinese Office Action dated Jun. 23, 2016; Appln. No. 201480005064.9.
Second Chinese Office Action dated Dec. 9, 2016; Appln. No. 201480005064.9.
Ludmila O. Cinteza, et al; "Diacyllipid Micelle-Based Nanocarrier for Magnetically Guided Delivery of Drugs in Photodynamic Therapy", Molecular Pharmaceutics. vol. 3, No. 4, pp. 415-423, Published on Web Apr. 19, 2006.
Gerelt-Ireedui Sengee, et al; "Photodynamic Effect of Water Soluble Piperazinium and Imidazolium Salts of HPPH on A549 Cancer Cells", Bull. Korean Chem. Soc. vol. 29, No. 12, pp. 2505-2508; Dec. 31, 2008.
Chinese Office Action dated Nov. 26, 2015; Appln. No. 201310046627.6.
Japanese Office Action dated May 31, 2016; Appln. No. 2015-555568.
Extended European Search Report, dated Jul. 4, 2016; Appln. No. 14749183.1-1460/2954898 PCT/CN2014070974.

* cited by examiner

*Primary Examiner* — Kevin E Weddington
(74) *Attorney, Agent, or Firm* — Ladas & Parry LLP

(57) ABSTRACT

Disclosed are a HPPH lyophilized powder injection for injection and the preparation method thereof. The HPPH lyophilized powder injection contains HPPH, auxiliary solvents, solubilizing agents, excipients, and pH adjusting agents. The HPPH lyophilized powder injection is loose and has good resolubility, low moisture, and good stability.

12 Claims, No Drawings

HPPH LYOPHILIZED POWDER INJECTION FOR INJECTION AND PREPARATION METHOD THEREOF

FIELD OF THE INVENTION

The present invention relates to the field of medicament, specifically to a HPPH lyophilized powder injection for injection and the preparation method thereof.

BACKGROUND OF THE INVENTION

Antitumor photosensitizer HPPH belongs to the second generation photosensitizer, which is a kind of chlorin compound extracted, purified and semi-synthesized from green plants by the researchers of Roswell Park Tumor Institute in US. The structure formula is as follows:

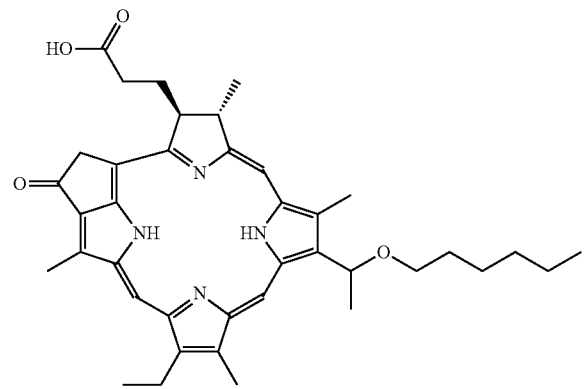 [SMILES: CCCCCCOC(C)c1c(C)c2cc3nc(c4c5[nH]c(cc6nc(cc1[nH]2)C(C)=C6CC)c(C)c5C(=O)C4)[C@@H](CCC(=O)O)[C@@H]3C]

HPPH has fairly well photodynamic activities, ideal action spectrum and good targeting as well as has high penetration rates to tumor tissues. In clinic, HPPH can be used in the treatment of lung cancer, esophageal carcinoma, head-face-neck cancer, bladder carcinoma, gastric cancer and many kinds of other solid tumors. Compared with the first generation photosensitizer, the phototoxicity of HPPH is obviously reduced and there is substantially no necessity for being protected from light. Further, the dosage is small and it is convenient to use, thus HPPH is a PDT photosensitizer for treating cancers with an extremely great market potential and it has become one hot topic in the research field of anticancer drugs recently. In foreign countries, the related Phase II clinical study has been conducted, but in China, the PDT market is nearly in blank and the present antitumor photosensitizer belongs to the first generation which has high toxicity and cost for treating. As a new generation photosensitizer, HPPH will surpass its competitive products and occupy beneficial position by virtue of its specific superiorities and relatively low price.

HPPH has fairly well anticancer effects, however, it has poor solubility in water and is unstable in water. It is reported that in the liquid injection used in the Phase II clinical study in foreign countries, during the process of preparing formulations of HPPH, excess feeds are required because of the solubility issue of the active component. Moreover, during the process of formulating a solution, the period of dissolving the active components is nearly 18 hours, and the storage condition for the obtained formulation is −20° C. as well as the term of validity is one year. Hence, such a liquid injection is not suitable for a large-scale manufacture and its application is extremely restricted. Further, it would bring about some improper influence to the safety and effectiveness of its clinical medication.

SUMMARY OF THE INVENTION

The objective of the present invention is to overcome defects of the present HPPH liquid injection including poor solubility during formulating, failure of feed in determined quantities and the relatively low stability of formulation. The present invention provides a stable HPPH lyophilized powder injection for injection, wherein such a lyophilized powder injection can be fed in determined quantities, the time for formulating the solution is short, and the formulation product can be stored merely in cold-storage, even if at room temperature, it can also be stored for a rather long time, that is, the stability has been greatly increased.

The present invention discloses a HPPH lyophilized powder injection for injection comprising HPPH, auxiliary solvents, solubilizing agents, excipients, and pH adjusting agents, wherein the weight percentages of HPPH, auxiliary solvents, solubilizing agents, and excipients are as follows:

| | |
|---|---|
| HPPH | 0.05%~3.50% |
| auxiliary solvents | 0.05%~0.50% |
| solubilizing agents | 0.80%~28.00% |
| excipients | 70.00%~99.00%. |

In a preferred embodiment, the weight percentages of HPPH, auxiliary solvents, solubilizing agents, and excipients are as follows:

| | |
|---|---|
| HPPH | 0.08%~2.50% |
| auxiliary solvents | 0.08%~0.25% |
| solubilizing agents | 0.95%~25.00% |
| excipients | 70.00%~99.00%. |

In a preferred embodiment, the present invention discloses a HPPH lyophilized powder injection for injection, wherein the proportions of each raw material are as follows:

| | |
|---|---|
| HPPH | 0.50~7.50 g |
| solvents | 30.00~150.00 g |
| auxiliary solvents | 0.50~0.65 g |
| solubilizing agents | 5.00~100.00 g |
| excipients | 300.00~500.00 g |
| pH adjusting agents | q.s., adjusting the pH value to 6.0~8.0 |
| water for injection | added until 5000 ml in total |
| Prepared in total | 1000 bottles. |

In another preferred embodiment, the present invention discloses a HPPH lyophilized powder injection for injection, wherein the proportions of each raw material are as follows:

| | |
|---|---|
| HPPH | 4.00~6.00 g |
| solvents | 100.00~150.00 g |
| auxiliary solvents | 0.51~0.56 g |
| solubilizing agents | 25.00~50.00 g |
| excipients | 350.00~400.00 g |
| pH adjusting agents | q.s., adjusting the pH value to 6.5~7.5 |
| water for injection | added until 5000 ml in total |
| Prepared in total | 1000 bottles. |

In which, the solvent in the above formulation is 95%~100% (v/v) ethanol.

In which, the auxiliary solvent in the above formulation is sodium carbonate. Preferably, during the process of preparing the formulation, the auxiliary solvent is dissolved in water for injection and used in the form of a solution.

In which, the solubilizing agents in the above formulation are polyoxyethylene castor oil (EL), tweens or polyethylene glycol stearate 15. Polyoxyethylene castor oil (EL) or polyethylene glycol stearate 15 is preferred.

In which, the excipients in the above formulation are mannitol, lactose or dextran. Mannitol is preferred.

In which, the pH adjusting agents in the above formulation are phosphoric acid, hydrochloric acid or acetic acid. Phosphoric acid is preferred. Preferably, during the process of preparing the formulation, the pH adjusting agent is dissolved in water for injection and used in the form of a solution.

The present invention also provides a method for preparing a HPPH lyophilized powder injection for injection comprising the following steps:

a) transferring a prescribed amount of excipient into a compounding tank filled with suitable amount of water for injection, stirring until dissolved, then obtaining Solution ①;

b) weighing and placing a prescribed amount of HPPH into the compounding tank, adding prescribed amounts of solvent, a solution of auxiliary solvent and a solubilizing agent, stirring until dissolved, then obtaining Solution ②; and c) adding Solution ② into Solution ①, stirring, adding water for injection until a prescribed volume, adding in drops the pH adjusting agent to adjust the pH value of the solution to 6.0~8.0, preferably 6.5~7.5; filtering and sterilizing the solution, followed by putting the solution into the liquid storage tank, subpackaging, partial stoppering lyophilizing, stoppering and packaging.

In which, the feeding sequence of formulating Solution ② in step b) is as follows: the prescribed amounts of solvent, a solution of auxiliary solvent and a solubilizing agent are added into HPPH successively. It is proved by the experiments that the effects of dissolving will be relatively well according to such a feeding sequence.

In which, the lyophilizing step in step c) includes:

1) pre-lyophilizing: pre-lyophilizing the products at −40~−50° C. for 2~4 hours to make the products frozen and compacted;

2) the first drying: after the pre-lyophilizing of the products, starting the vacuum pump to evacuate until the degree of vacuum reaches 20~30 Pa, increasing the temperature of the products to reach −5° C. and maintaining for 27-31 hours; and 3) desorption drying: gradually warming up the products to the temperature of 20° C., and maintaining for 3~5 hours.

The obtained HPPH lyophilized powder injection for injection prepared by the present invention is formulated reasonably, and the time for formulating the solution is relatively short. Further, the obtained formulation is loose and has good resolubility, low moisture, good stability, and low dark-toxicity as well as high photosensitivity.

EXAMPLES

The present invention will be further illustrated by the following examples. It should be noted that the following examples are only intended to illustrate the present invention rather than to limit the scope of the present invention in any way.

Example 1

| | |
|---|---|
| HPPH | 5.0 g |
| absolute alcohol | 150.0 g |
| sodium carbonate | 0.56 g |
| polyoxyethylene castor oil (EL) | 50.0 g |
| mannitol | 300.0 g |
| phosphoric acid | q.s., adjusting the pH value to 7.0 |
| water for injection | added until 5000 ml in total |
| Prepared in total | 1000 bottles | a) transferring a prescribed amount of mannitol into a compounding tank filled with 2000 ml of water for injection, stirring until dissolved, then obtaining Solution ①;

b) weighing and placing a prescribed amount of HPPH into the compounding tank, adding a prescribed amount of absolute alcohol, stirring, adding prescribed amounts to of sodium carbonate solution and polyoxyethylene castor oil, further stirring until dissolved, then obtaining Solution ②; and c) adding Solution ② into Solution ①, stirring, adding water for injection to reach 5000 ml, then adding in drops the phosphoric acid aqueous solution to adjust the pH value of the solution to 7.0; filtering and sterilizing the solution, followed by putting is the solution into the liquid storage tank, subpackaging, partial stoppering, lyophilizing, stoppering and packaging. In which, the lyophilizing step is as follows:

1) pre-lyophilizing: pre-lyophilizing the products at −40~−50° C. for 3 hours to make the products frozen and compacted;

2) the first drying: after the pre-lyophilizing of the products, starting the vacuum pump to evacuate until the degree of vacuum reaches 20~30 Pa, increasing the temperature of the products to −5° C. and maintaining for 28 hours; and 3) desorption drying: gradually warming up the products to reach the temperature of 20° C., and maintaining for 5 hours.

Example 2

| | |
|---|---|
| HPPH | 1.0 g |
| 96% alcohol | 30 g |
| sodium carbonate | 0.50 g |
| Tween 80 | 5.00 g |
| dextran | 500 g |
| phosphoric acid | q.s., adjusting the pH value to 6.5 |
| water for injection | added until 5000 ml in total |
| Prepared in total | 1000 bottles | a) transferring a prescribed amount of dextran into a compounding tank filled with 2500 ml of water for injection, stirring until dissolved, then obtaining Solution ①;

b) weighing and placing a prescribed amount of HPPH into the compounding tank, adding a prescribed amount of 96% alcohol, stirring, adding prescribed amounts of sodium carbonate solution and Tween 80, further stirring until dissolved, then obtaining Solution ②; and c) adding Solution ② into Solution ①, stirring, adding water for injection to reach 5000 ml, then adding in drops the phosphoric acid aqueous solution to adjust the pH value of the solution to 6.5; filtering and sterilizing the solution, followed by putting the solution into the liquid storage tank, subpackaging, partial stoppering, lyophilizing, stoppering and packaging. In which, the lyophilizing step is as follows:

1) pre-lyophilizing: pre-lyophilizing the products at −40~−50° C. for 3.5 hours to make the products frozen and compacted;

2) the first drying: after the pre-lyophilizing of the products, starting the vacuum pump to evacuate until the degree of vacuum reaches 20~30 Pa, improving the temperature of the products to −5° C. and maintaining for 29 hours; and 3) desorption drying: gradually warning up the products to reach the temperature of 20° C., and maintaining for 4 hours.

Example 3

| | |
|---|---|
| HPPH | 7.5 g |
| 95% alcohol | 100 g |
| sodium carbonate | 0.63 g |
| polyethylene glycol stearate 15 | 100 g |
| mannitol | 500 g |
| phosphoric acid | q.s., adjusting the pH value to 7.8 |
| water for injection | added until 5000 ml |
| Prepared in total | 1000 bottles | a) transferring a prescribed amount of mannitol into a compounding tank filled with 3000 ml of water for injection, stirring until dissolved, then obtaining Solution ①;

b) weighing and placing a prescribed amount of HPPH into the compounding tank, adding a prescribed amount of 95% alcohol, stirring, adding prescribed amounts of sodium carbonate solution and polyethylene glycol stearate 15, further stirring until dissolved, then obtaining Solution ②; and c) adding Solution ② into Solution ①, stirring, adding water for injection to reach 5000 ml, then adding in drops the phosphoric acid aqueous solution to adjust the pH value of the solution to 7.8; filtering and sterilizing the solution, followed by putting the solution into the liquid storage tank, subpackaging, partial stoppering, lyophilizing, stoppering and packaging. In which, the lyophilizing step is as follows:

1) pre-lyophilizing: pre-lyophilizing the products at −40~−50° C. for 4 hours to make the products frozen and compacted;

2) the first drying: after the pre-lyophilizing of the products, starting the vacuum pump to evacuate until the degree of vacuum reaches 20~30 Pa, increasing the temperature of the products to −5° C. and maintaining for 31 hours; and 3) desorption drying: gradually warming up the products to reach the temperature of 20° C., and maintaining for 3 hours.

Example 4

| | |
|---|---|
| HPPH | 5.0 g |
| 96% alcohol | 80.0 g |
| sodium carbonate | 0.55 g |
| polyoxyethylene castor oil (EL) | 30.0 g |
| mannitol | 400.0 g |
| phosphoric acid | q.s. |
| water for injection | added until 5000 ml in total |
| Prepared in total | 1000 bottles | a) transferring a prescribed amount of mannitol into a compounding tank filled with 4000 ml of water for injection, stirring until dissolved, then obtaining Solution ①;

b) weighing and placing a prescribed amount of HPPH into the compounding tank, adding a prescribed amount of 96% alcohol, stirring, adding prescribed amounts of sodium carbonate solution and polyoxyethylene castor oil, further stirring until dissolved, then obtaining Solution ②; and c) adding Solution ② into Solution ①, stirring, adding water for injection to reach 5000 ml, then adding in drops the phosphoric acid aqueous solution to adjust the pH value of the solution to 7.3; filtering and sterilized the solution, followed by putting the solution into the liquid storage tank, subpackaging, partial stoppering, lyophilizing, stoppering and packaging. In which, the lyophilizing step is as follows:

1) pre-lyophilizing: pre-lyophilizing the products at −40~−45° C. for 2.5 hours to make the products frozen and compacted;

2) the first drying: after the pre-lyophilizing of the products, starting the vacuum pump to evacuate until the degree of vacuum reaches 20~30 Pa, increasing the is temperature of the products to −5° C. and maintaining for 29 hours; and 3) desorption drying: gradually warming up the products to reach the temperature of 20° C., and maintaining for 4 hours.

Example 5 Study of Stability

Place the lyophilized powder injections obtained by Examples 1-4 as well as the bulk solution before being lyophilized respectively under the conditions of 40° C. and 5° C. Conduct the study of stability, and the measured data about stability are as follows:

| | | Total Impurity % | | | | |
|---|---|---|---|---|---|---|
| Sample | Temperature | 0 day | 1 week | 2 weeks | 4 weeks | 6 weeks |
| lyophilized powder injection of Example 1 | 40° C. | 0.33 | 0.46 | 0.61 | 0.74 | 1.18 |
| | 5° C. | 0.33 | 0.35 | 0.44 | 0.48 | 0.51 |
| unlyophilized bulk solution of Example 1 | 40° C. | 0.33 | 1.43 | 2.17 | 2.21 | 2.20 |
| | 5° C. | 0.33 | 0.59 | 0.75 | 0.92 | 1.68 |
| lyophilized powder injection of Example 2 | 40° C. | 0.31 | 0.43 | 0.78 | 0.85 | 1.42 |
| | 5° C. | 0.31 | 0.35 | 0.41 | 0.52 | 0.62 |
| unlyophilized bulk solution of Example 2 | 40° C. | 0.38 | 2.30 | 2.75 | 3.14 | 4.01 |
| | 5° C. | 0.38 | 0.77 | 0.85 | 1.19 | 1.82 |
| lyophilized powder injection of Example 3 | 40° C. | 0.32 | 0.41 | 0.68 | 1.01 | 1.22 |
| | 5° C. | 0.32 | 0.34 | 0.35 | 0.47 | 0.55 |
| unlyophilized bulk solution of Example 3 | 40° C. | 0.31 | 1.34 | 1.95 | 2.64 | 2.57 |
| | 5° C. | 0.31 | 0.45 | 0.90 | 1.28 | 1.75 |
| lyophilized powder injection of Example 4 | 40° C. | 0.35 | 0.66 | 0.72 | 0.96 | 1.11 |
| | 5° C. | 0.35 | 0.35 | 0.45 | 0.48 | 0.50 |
| unlyophilized bulk solution of Example 4 | 40° C. | 0.37 | 1.92 | 2.02 | 2.03 | 2.22 |
| | 5° C. | 0.37 | 0.48 | 0.73 | 1.29 | 1.66 |

It can be seen from the above data that, both the increasing ranges and the increasing rates of the impurities of lyophilized powder injections are far below those of the bulk solution before being lyophilized. Thus, the stability of the lyophilized powder injection is obviously higher than the stability of the bulk solution before being lyophilized. Based on a comprehensive consideration of the safety and effectiveness of the formulation, the lyophilized powder injection would be chosen as a preferred formulation.

Example 6 Study of Stability

According to the proportions and technology of the formulations in Examples 2 and 4, prepare another three batches of lyophilized powder injections. Place every batch at 5° C. and conduct the study of stability. The measured data about stability are as follows:

| Sample | Batch | 0 day | 3 months | 6 months | 12 months | 18 months | 24 months |
|---|---|---|---|---|---|---|---|
| lyophilized | Batch 1 | 0.25 | 0.26 | 0.30 | 0.34 | 0.35 | 0.39 |
| powder injection | Batch 2 | 0.30 | 0.32 | 0.35 | 0.38 | 0.40 | 0.45 |
| of Example 2 | Batch 3 | 0.31 | 0.33 | 0.37 | 0.40 | 0.41 | 0.43 |
| lyophilized | Batch 1 | 0.24 | 0.26 | 0.29 | 0.30 | 0.31 | 0.35 |
| powder injection | Batch 2 | 0.29 | 0.30 | 0.33 | 0.35 | 0.39 | 0.39 |
| of Example 4 | Batch 3 | 0.20 | 0.22 | 0.28 | 0.31 | 0.31 | 0.34 |

Total Impurity %

It can be seen from the above data that, all batched of the lyophilized powder injections have uniform qualities, and the repeatability among the batches is good. Under the condition of 5° C., the increasing rates of the impurities within 24 months are rather slow, thus the stability of the product is high.

The invention claimed is:

1. A HPPH lyophilized powder injection, comprising HPPH, auxiliary solvents, solubilizing agents, excipients and pH adjusting agents, wherein the weight percentages of HPPH, auxiliary solvents, solubilizing agents, and excipients are as follows:

| HPPH | 0.05%~3.50% |
|---|---|
| auxiliary solvents | 0.05%~0.50% |
| solubilizing agents | 0.80%~28.00% |
| excipients | 70.00%~99.00%. |

2. The HPPH lyophilized powder injection according to claim 1, wherein the weight percentages of HPPH, auxiliary solvents, solubilizing agents, and excipients are:

| HPPH | 0.08%~2.50% |
|---|---|
| auxiliary solvents | 0.08%~0.25% |
| solubilizing agents | 0.95%~25.00% |
| excipients | 70.00%~99.00%. |

3. A HPPH lyophilized powder injection, wherein the proportions of each raw material are:

| HPPH | 0.50~7.50 g |
|---|---|
| solvents | 30.00~150.00 g |
| auxiliary solvents | 0.50~0.65 g |
| solubilizing agents | 5.00~100.00 g |
| excipients | 300.00~500.00 g |
| pH adjusting agents | q.s., adjusting the pH value to 6.0~8.0 |
| water for injection | added until 5000 ml in total |
| prepared in total | 1000 bottles. |

4. The HPPH lyophilized powder injection according to claim 3, wherein the proportions of each raw material are:

| HPPH | 4.00~6.00 g |
|---|---|
| solvents | 100.00~150.00 g |
| auxiliary solvents | 0.51~0.56 g |
| solubilizing agents | 25.00~50.00 g |
| excipients | 350.00~400.00 g |
| pH adjusting agents | q.s., adjusting the pH value to 6.5~7.5 |
| water for injection | added until 5000 ml in total |
| prepared in total | 1000 bottles. |

5. The HPPH lyophilized powder injection according to claim 3, wherein the solvent is 95%~100% (v/v) ethanol.

6. The HPPH lyophilized powder injection according to claim 1, wherein the auxiliary solvent is sodium carbonate.

7. The HPPH lyophilized powder injection according to claim 1, wherein the solubilizing agent is polyoxyethylene castor oil, tweens or polyethylene glycol stearate 15.

8. The HPPH lyophilized powder injection according to claim 1, wherein the excipient is mannitol, lactose or dextran.

9. The HPPH lyophilized powder injection according to claim 1, wherein the pH adjusting agent is phosphoric acid, hydrochloric acid or acetic acid.

10. The HPPH lyophilized powder injection according to claim 7, wherein the solubilizing agent is polyoxyethylene castor oil or polyethylene glycol stearate 15.

11. The HPPH lyophilized powder injection according to claim 8, wherein the excipient is mannitol.

12. The HPPH lyophilized powder injection according to claim 9, wherein the pH adjusting agent is phosphoric acid.

* * * * *